(12) United States Patent
Miyaoka (10) Patent No.: US 9,589,759 B2
(45) Date of Patent: Mar. 7, 2017

(54) X-RAY GENERATOR

(71) Applicant: SHIMADZU CORPORATION, Kyoto-shi, Kyoto (JP)

(72) Inventor: Akihiro Miyaoka, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 212 days.

(21) Appl. No.: 14/614,781

(22) Filed: Feb. 5, 2015

(65) Prior Publication Data

US 2015/0279608 A1 Oct. 1, 2015

(30) Foreign Application Priority Data

Mar. 28, 2014 (JP) ................................. 2014-068501

(51) Int. Cl.
*H01J 35/02* (2006.01)
*H01J 35/16* (2006.01)
(Continued)

(52) U.S. Cl.
CPC ................ *H01J 35/16* (2013.01); *A61B 6/40* (2013.01); *H01J 1/88* (2013.01); *H01J 19/56* (2013.01);
(Continued)

(58) Field of Classification Search
CPC .. H05G 1/00; H05G 1/02; H05G 1/04; H05G 1/26; H05G 1/52; H01J 1/00; H01J 1/02; H01J 1/18; H01J 1/36; H01J 1/40; H01J 1/46; H01J 1/88; H01J 5/00; H01J 5/02; H01J 5/04; H01J 5/12; H01J 5/18;
(Continued)

(56) References Cited

U.S. PATENT DOCUMENTS 2,209,963 A * 8/1940 Du Mond ............... H01J 35/26
   313/148
2,290,226 A * 7/1942 Du Mond ............... H01J 35/14
   313/148
(Continued)

FOREIGN PATENT DOCUMENTS

JP 2009-43741 A 2/2009
JP 2011-113705 A 6/2011

OTHER PUBLICATIONS

Office Action dated Jul. 29, 2016, issued in counterpart Chinese application No. 201510080168.2, with English translation. (9 pages).

*Primary Examiner* — Anastasia Midkiff
(74) *Attorney, Agent, or Firm* — Westerman, Hattori, Daniels & Adrian, LLP (57) ABSTRACT

An X-ray generator is provided using a transmission type target having a long life span, where it is possible to change the point for generating X-rays on the surface of the target while maintaining the vacuum chamber in a high vacuum state. A portion of a vacuum chamber 1 that includes a target 2 is linked to a main body portion 1a of the chamber through a linking member 5 as a movable chamber portion 1b. A fixed anode 12 is provided between the target 2 and the electrode 10 at the final stage from among a group of electrodes 8, 9 and 10 for electrostatically accelerating and converging electrons from an electron source 7 and is fixed to the main body portion 1a of the chamber in order to prevent the form of the electrical field from changing when the movable chamber portion 1b is shifted.

4 Claims, 5 Drawing Sheets (51) Int. Cl.

| | |
|---|---|
| *H01J 1/88* | (2006.01) |
| *H01J 19/56* | (2006.01) |
| *H01J 37/16* | (2006.01) |
| *H05G 1/04* | (2006.01) |
| *A61B 6/00* | (2006.01) |
| *H01J 5/02* | (2006.01) |
| *H01J 1/40* | (2006.01) |
| *H01J 5/04* | (2006.01) |
| *H01J 35/04* | (2006.01) |
| *H05G 1/02* | (2006.01) |
| *H01J 35/14* | (2006.01) |
| *H01J 35/28* | (2006.01) |

(52) U.S. Cl.
CPC .............. *H01J 35/02* (2013.01); *H01J 37/16* (2013.01); *H05G 1/04* (2013.01); *A61B 6/44* (2013.01); *A61B 2560/0406* (2013.01); *H01J 1/40* (2013.01); *H01J 5/02* (2013.01); *H01J 5/04* (2013.01); *H01J 35/04* (2013.01); *H01J 35/14* (2013.01); *H01J 35/28* (2013.01); *H01J 2235/083* (2013.01); *H01J 2235/087* (2013.01); *H01J 2235/16* (2013.01); *H01J 2235/163* (2013.01); *H01J 2235/186* (2013.01); *H05G 1/02* (2013.01)

(58) Field of Classification Search
CPC ........ H01J 5/20; H01J 5/22; H01J 5/48; H01J 19/00; H01J 19/54; H01J 19/56; H01J 19/64; H01J 35/00; H01J 35/02; H01J 35/025; H01J 35/04; H01J 35/08; H01J 35/14; H01J 35/16; H01J 35/165; H01J 35/18; H01J 37/00; H01J 37/16; H01J 37/165; H01J 2235/00; H01J 2235/08; H01J 2235/081; H01J 2235/083; H01J 2235/086; H01J 2235/087; H01J 2235/16; H01J 2235/161; H01J 2235/163; H01J 2235/186; A61B 6/00; A61B 6/40; A61B 6/44; A61B 2560/00; A61B 2560/04; A61B 2560/0406

See application file for complete search history.

(56) References Cited

U.S. PATENT DOCUMENTS

| | | | | |
|---|---|---|---|---|
| 2,922,904 | A | | 1/1960 | Zunick |
| 3,689,790 | A | * | 9/1972 | Haas ................. H01J 35/24 313/30 |
| 3,737,698 | A | * | 6/1973 | Carter ................ H01J 35/02 378/124 |
| 3,753,020 | A | * | 8/1973 | Zingaro .............. H01J 35/12 313/149 |
| 3,794,872 | A | * | 2/1974 | Haas ................. H01J 35/24 313/32 |
| 3,835,341 | A | * | 9/1974 | Zingaro .............. H01J 35/18 378/140 |
| 2005/0190887 | A1 | * | 9/2005 | Kim ................... H01J 35/24 378/125 |
| 2014/0247921 | A1 | * | 9/2014 | Parker ............... H01J 35/10 378/125 |
| 2014/0314209 | A1 | * | 10/2014 | Parker ............... H01J 35/10 378/140 |

* cited by examiner

Prior Art

FIG. 5

Prior Art

X-RAY GENERATOR

CROSS-REFERENCE TO RELATED APPLICATIONS

This application claims priority to Japanese Patent Application No. 2014-068501 filed Mar. 28, 2014, the subject matter of which is incorporated herein by reference in entirety.

BACKGROUND OF THE INVENTION

1. Field of the Invention

The present invention relates to an X-ray generator to be used for an X-ray inspection device for industrial or medical use or for any of various types of X-ray spectrometers and measurement devices using the diffraction or refraction of X-rays, and in particular, to a transmission type X-ray generator where X-rays are generated by colliding electrons with a target inside a vacuum chamber and are emitted to the outside of the chamber mainly in the direction in which the electrons travel.

2. Description of Related Art

X-ray generators of the type for generating X-rays by colliding electrons with a target inside a vacuum chamber include those using a reflective type target from which X-rays are taken out in a direction that is different from the direction in which the electrons travel and those using a transmission type target from which X-rays are taken out in approximately the same direction in which the electrons travel. Transmission type targets are usually formed of a thin film, and therefore, have a shorter life span as compared to reflective type targets that can be made of a bulk material. In order to make the life span of the transmission type targets longer, various ways and means have been figured out so that a number of points for generating X-rays can be set in the target plane, that is to say, the point that is irradiated with an electron beam can be changed on the target.

Figure 4:
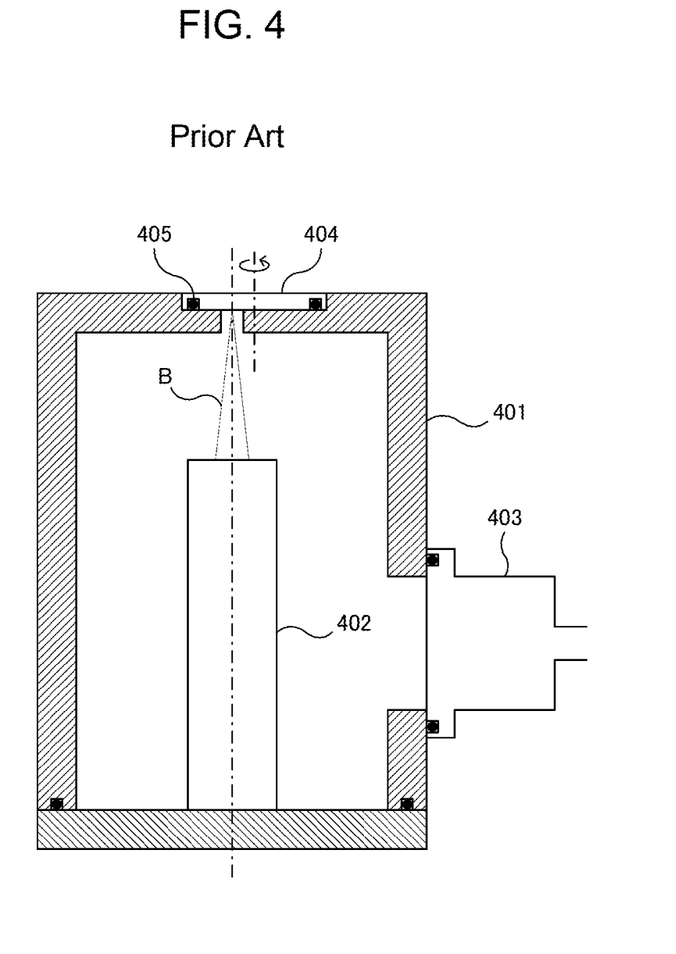
FIG. 4 is a diagram illustrating the structure of an X-ray generator using an open type vacuum chamber.

As shown in FIG. 4, an open type X-ray generator using a transmission type target contains a so-called electron gun 402 having an electron source and a group of electrodes within a vacuum chamber 401, and is formed so that the inside of the vacuum chamber 401 can be vacuumed at any time by means of a vacuum pump 403. An X-ray emitting window 404 that is formed so as to integrate a target is air-tightly supported by the vacuum chamber 401 using an O-ring 405 that is located eccentrically with respect to the trajectory of the electron beam B from the electron gun 402. When the X-ray emitting window 404 is rotated in this structure, a number of points for generating X-rays can be set relatively easily in the target plane.

Figure 5:
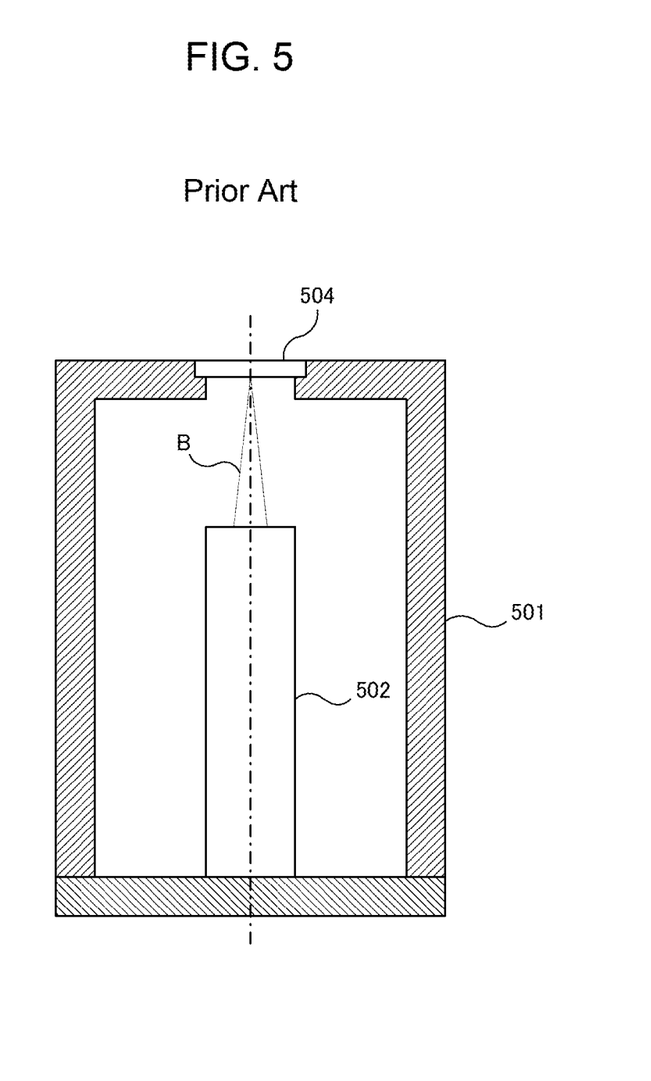
FIG. 5 is a diagram illustrating the structure of an X-ray generator using a closed type vacuum chamber.

In contrast, as shown in FIG. 5, in a sealed type, an X-ray emitting window 504 that is formed so as to integrate a target is air-tightly fixed to a vacuum chamber 501 through welding or brazing, and therefore, cannot be rotated unlike the described above type. In this sealed type structure, the point on the target that is irradiated with the electron beam B from the electron gun 502 cannot be changed, and therefore, the following measures have been proposed.

One measure is to provide a permanent magnet that is movable along the periphery outside the vacuum chamber so that the magnetic field created within the vacuum chamber by the permanent magnet can be changed when the location of the permanent magnet is changed. In accordance with this technology, the trajectory of the electron beam can be changed so that the point irradiated with the electron beam can be changed on the target (see Patent Document 1).

Another measure is to provide a vacuum chamber with such a structure that a main body portion to which an electron gun is fixed and a target support portion to which an X-ray emitting window that is integrated with a target is fixed are formed of different members and these are linked through a linking body so as to be displaceable relative to each other. In accordance with this technology, the target support portion can be inclined to any direction relative to the trajectory of the electron beam from the electron gun so that the point irradiated with the electron beam can be changed on the target (see Patent Document 2).

PRIOR ART DOCUMENTS

Patent Documents

Patent Document 1: Japanese Unexamined Patent Publication 2009-043741
Patent Document 2: Japanese Unexamined Patent Publication 2011-113705

SUMMARY OF THE INVENTION

1. Problem to Be Solved by the Invention

In accordance with the technology in Patent Document 1, the trajectory of the electron beam is changed within the vacuum chamber in order to provide a number of points for generating X-rays in the target plane in the X-ray generator using a transmission type target, the absolute position of the point for generating X-rays shifts in the fixed vacuum chamber whenever the point for generating X-rays is changed. That is to say, the focal point of the X-rays shifts.

Here, it is not preferable for the focal point to shift in an X-ray inspection device because the region to be seen through changes and various readjustments become necessary including reconstruction of various types of parameters for the system of the device and realignments of the relative positions of the components of the device.

Accordingly, microscopic adjustments of the location of the vacuum chamber or the entirety of the X-ray generator become necessary whenever the point for generating X-rays is changed in the target plane in order to solve the above described problem by maintaining the position of the focal point of X-ray constant.

Meanwhile, in accordance with the technology in Patent Document 2, where the trajectory of the electron beam is fixed within the vacuum chamber and a portion of the vacuum chamber including the X-ray emitting window with which the target is integrated (hereinafter referred to as the target member) is shifted relative to the trajectory of the electron beam, the focal point does not appear to be shifted unlike the above. In reality, however, the focal point shifts in a microscopic focal point X-ray generator, which is microscopic but cannot be overlooked.

In many cases, an electron converging system for electrostatically converging electrons by means of an electrical field created by a number of electrodes is used for a sealed type vacuum chamber of a microscopic focal point X-ray generator. In the case where this is made compact, the anode for accelerating electrons is usually used also as the target member for generating X-rays. That is to say, the target member is used as the anode at the same time.

In the technology disclosed in Patent Document 2, when a portion of the vacuum chamber containing a target member is displaced relative to the main body portion of the chamber, the unevenness of the inner surface within the vacuum chamber changes, which changes the form of the electrical field inside the vacuum chamber. The trajectory of the electron beam changes together with this change in the form of the electrical field, and thus, the absolute position of the point for generating X-rays shifts, namely the focal point shifts. Accordingly, in accordance with the technology in Patent Document 2 as well, an adjustment for microscopically shifting the entirety of the X-ray generator is necessary, whenever the point for generating X-rays changes in the target plane, in order to maintain the position of the focal point of X-ray constant.

In addition, the target generates a large amount of heat as electrons collide with the target when the target member is irradiated with an electron beam over a long period of time, and thus, the temperature of the target member and its vicinity increases and induces thermal expansion. In either system in Patent Document 1 where the center axis of the internal structure of the vacuum chamber and the trajectory of the electron beam are not the same or in Patent document 2 where the internal structure of the vacuum chamber is asymmetric with respect to the trajectory of the electron beam in the vicinity of the target member, the form of the electrical field within the vacuum chamber changes as a result of the thermal expansion, which causes the focal point to chronologically shift. That is to say, in the case where electrons start being emitted from the device that has just been turned on, the thermal expansion continues shifting the focal point until thermal equilibrium is achieved. This shift in the focal point due to the thermal expansion causes the following problem.

In the case where images are taken with a CT apparatus over a long period of time, the quality of the obtained CT images deteriorates and the performance of the apparatus is affected when the focal point shifts while images are being taken. Even when the focal point shifts in an order of μm, it is not preferable for the microfocus X-ray generator, for example.

The present invention is provided in view of such a situation, and an object thereof is to provide an X-ray generator using a transmission type target having such a structure as to be applicable to a sealed type device without losing the vacuum degree in the vacuum chamber, wherein a number of points for generating X-rays are set on the target surface so that the life span of the target can be made longer, and at the same time, the focal point barely shifts when the point for generating X-rays is changed so that thermal expansion during the usage over a long period of time can cause the focal point to shift as little as possible.

2. Means for Solving Problem

In order to achieve the above described object, the X-ray generator according to the present invention is provided with: a vacuum chamber having an X-ray emitting window with which a target is integrated; and an electron source and a group of electrodes placed within the vacuum chamber, wherein each electrode has a predetermined potential difference relative to the electron source or the vacuum chamber so that electrons from the above described electron source are accelerated and converged by an electrical field created within the vacuum chamber so as to irradiate the above described target, and thus, X-rays can be generated so as to be taken out to the outside through the above described X-ray emitting window, and is characterized in that a portion of the above described vacuum chamber including the above described emitting window is linked to a main body portion of the vacuum chamber through a linking member so as to be movable, and an anode having a hole through which electrons transmit and having the same potential as the vacuum chamber is provided between the electrode at the final stage of the above described group of electrodes and the above described target within the above described vacuum chamber in such a state as to be fixed to the main body portion of the vacuum chamber (claim 1).

Here, the present invention can preferably adopt a configuration wherein the above described anode is provided in close proximity to the above described target (claim 2).

In addition, it is desirable for the present invention to adopt a configuration wherein a member made of a light element of which the atomic number is no greater than 13 is used for the above described anode in at least a range that has a possibility that reflected electrons may collide with (claim 3).

Furthermore, the present invention can adopt a configuration wherein the above described linking member is a portion of the vacuum chamber including the above described X-ray emitting window, which is linked to the above described main body portion of the vacuum chamber so as to be translatable, and the portion of the vacuum chamber including the above described X-ray emitting window makes contact with the outside of the above described vacuum chamber, of which the contact state can be regulated so as to be translatable relative to the above described main body portion of the vacuum chamber by a regulating member that is provided in the X-ray generator (claim 4).

According to the present invention, a portion of the vacuum chamber including the X-ray emitting window to which the target is integrated is linked to the main body portion of the vacuum chamber through a linking member so as to be movable so that the target can be shifted relative to the trajectory of the electron beam, which makes it possible to provide a number of points for generating X-rays in the target plane. An anode having the same potential as the target and the X-ray emitting window to which the target is integrated is provided at the front stage thereof so as to be fixed to the main body portion of the vacuum chamber. As a result, the change in the form of the electrical field accompanying the shift of the portion of the vacuum chamber including the X-ray emitting window as well as change in the form of the electrical field accompanying an increase in the temperature due to usage over a long period of time can be avoided respectively.

That is to say, the present invention is the same as of the technology in Patent Document 2 in that the trajectory of the electron beams is fixed and the target is shifted relative to the trajectory, which makes it possible to provide a number of points for generating X-rays in the lane of the target. In the technology in Patent Document 2, however, a portion of the vacuum chamber including the target member that forms the anode is displaced relative to the main body portion of the chamber so that the form of the electrical field can be changed together with the change in the unevenness of the inner surface of the vacuum chamber, which causes the trajectory of the electron beam to be changed so as to shift the focal point. In contrast, according to the present invention, an anode having the same potential is separately provided at the front stage of the target member in such as state as to be fixed to the main body side of the vacuum chamber. As a result, the form of the electrical field within the vacuum chamber is determined by the electron source, the group of the electrodes and the anode that is additionally provided according to the present invention, and thus the form of the electrical field within the vacuum chamber is not substantially changed and the trajectory of the electron beam is barely changed even when the portion of the vacuum chamber including the target member is shifted.

In the configuration of the present invention where the target can be shifted, the thermal expansion occurs in an asymmetric manner relative to the trajectory of the electron beam as the result of the increase in the temperature when the target is irradiated with the electron beam over a long period of time, which is the same as in the case in Patent Document 2. In the present invention, however, an anode having the same potential is provided at the front stage of the target so as to be fixed to the main body of the vacuum chamber, and thus, the form of the electrical field does not change to such an extent as to affect the trajectory of the electron beam due to the fact that there is no potential difference between the anode and the target. Therefore, the amount of the shift of the focal point after the usage over a long period of time would be negligible in the microfocus X-ray generator.

In addition, when the anode that is fixed to the main body portion of the vacuum chamber between the target and the electrode at the final stage is provided in close proximity to the target as in the invention according to claim 2, there is an advantage that the diameter of the electron beam spot that converges on the surface of the target can be made smaller.

Furthermore, a portion of the electron beam with which the target is irradiated is reflected so as to collide with the anode, which is then generates X-rays. This would cause the image quality to diminish in an X-ray generator for industrial use. Therefore, it is desirable as in the invention according to claim 3 for a member made of a light element of which the atomic number is no greater than 13, for example beryllium, carbon or aluminum, to be used for the anode in at least a range that has a possibility that reflected electrons may collide with.

Moreover, when the point for generating X-rays is shifted in the target plane by translating a portion of the vacuum chamber relative to the main body portion of the vacuum chamber through the regulation of the positions of the translatable linking member and the regulating member provided outside the vacuum chamber as in the invention according to claim 4, the amount of eccentricity of the target from the trajectory of the electron beam can be made without failure as compared to the conventional technology, and at the same time, the number of the settings of the point for generating X-rays can be increased, and as a result, the life span of the target can be further extended.

3. Effects of the Invention

According to the present invention, a portion of the vacuum chamber including the X-ray emitting window with which the target is integrated is linked to the main body portion of the vacuum chamber by means of a linking member so as to be movable so that the point in the target irradiated with the electron beam can be changed when the portion of the vacuum chamber moves. As a result, a number of points for generating X-rays can be set on the surface of the target, of which the life span can thus be extended. At the same time, an anode having the same potential as the target is provided between the target and the electrode at the final stage of the group of electrodes for accelerating and converging the electron beam so as to be fixed to the main body portion of the chamber. As a result, the form of the electrical field within the vacuum chamber does not change when the target and the part of the vacuum chamber including the X-ray emitting window are shifted, and thus, the focal point of the X-ray does not substantially shifts when the point for generating X-rays is changed.

In addition, an anode having the same potential as the target is provided between the target and the group of electrodes so that the form of the electrical field can be prevented from changing due to the thermal expansion when the temperature of the vacuum chamber in the vicinity of the target increases due to the usage over a long period of time, and as a result, the focal point of the X-ray can be prevented from shifting as much as possible due to the usage over a long period of time.

As described above, the present invention can be applied to a closed type X-ray generator using a transmission type target so that the shift of the focal point of X-ray when the point of generating X-rays is changed and the chronological change of the focal point of X-ray during the usage over a long period of time can be suppressed to such a degree as can be neglected for practical use, and thus, the life span of the target can be extended.

DETAILED DESCRIPTION OF EMBODIMENTS

Figure 1:
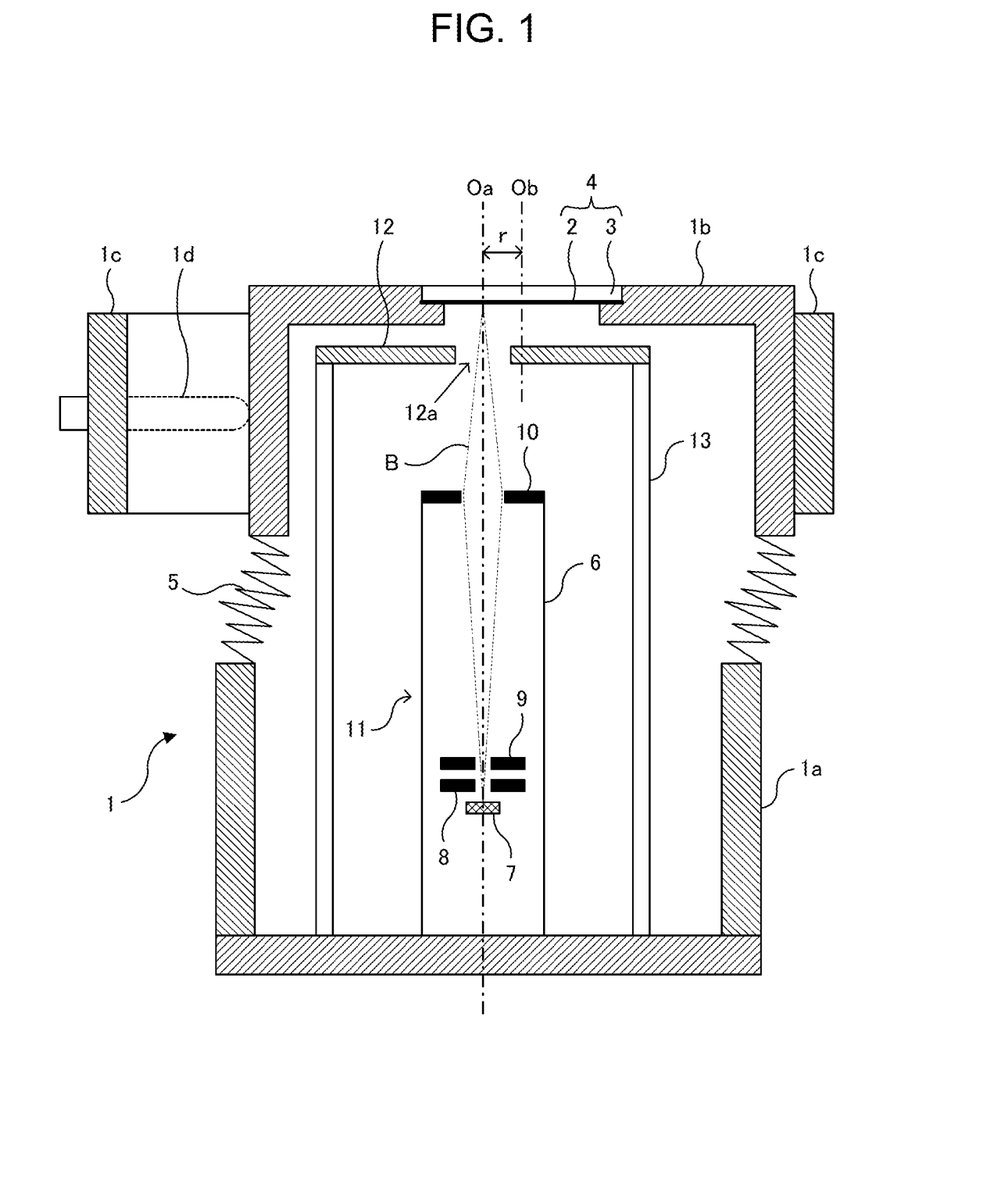
FIG. 1 is a schematic cross sectional diagram showing an embodiment of the present invention.

In the following, the embodiments of the present invention are described in reference to the drawings. FIG. 1 is a schematic cross sectional diagram showing an embodiment of the present invention.

A vacuum chamber 1 is of a closed type, and a target member 4 formed of a target 2 in a thin film form that is integrated with an X-ray emitting window 3 is fixed to the top of the vacuum chamber 1. The vacuum chamber 1 is formed of a movable chamber portion 1b on the upper side and a main body portion 1a of the chamber on the lower side. The movable chamber portion 1b contains the point where the target member 4 is provided and is linked to the main body portion 1a of the chamber through a linking member 5. The linking member 5 is formed of a member such as a welded bellow that allows the movable chamber portion 1b to translate relative to the main body portion 1a of the chamber, in other words, allows the movable chamber portion 1b to move in the direction perpendicular to the center axis Oa of the main body portion 1a of the chamber.

A stopper 1c is provided outside the vacuum chamber 1 so as to surround the movable chamber portion 1b. The stopper 1c is an annular member, and can be in a state as being held at a certain distance away from and parallel to the main body portion 1a of the chamber where the side opposite to the movable chamber portion 1b is made to make close contact with the stopper 1c when a screw 1d is tightened through the stopper 1c to press the movable chamber portion 1b of which the position is also regulated. This mechanism for pressing the side of the movable chamber portion 1b is shown in the figure. The target member 4 is provided along the center axis Ob of the movable chamber portion 1b. When the movable chamber portion 1b is made to make contact with the stopper 1c, an eccentric state is achieved where the center of the target member 4 is at a regulated distance r away from the center axis Oa of the main body portion 1a of the chamber.

The stopper 1c is the regulating member in the present invention. The regulating member for translating the movable chamber 1b is not limited to the above described structure, and may be formed of, for example, a flange member provided in the movable chamber portion and a support member having a groove that supports the flange member in a slidable fashion.

The vacuum chamber 1 contains an electron gun 11 having an electron source 7 and three electrodes 8, 9 and 10 within a housing 6 in such a state that the lower end of the electron gun 11 is fixed to the main body portion 1a of the chamber, which has the same axis as the center axis Oa. The power is supplied to the electron source 7 in order to generate hot electrons through heating, and at the same time, a negative high voltage is applied to the electron source 7 and each of the electrodes 8, 9 and 10 in accordance with the function thereof. The vacuum chamber 1 and the target member 4 that is fixed to the vacuum chamber 1 are electrically grounded.

That is to say, a high voltage of minus several tens of kV to minus one hundred and several tens of kV relative to the ground potential is applied to the electron source 7 in order to accelerate the electrons travelling towards the target. The electrode 8 functions as a grid for preventing the electrons generated from the electron source 7 from spreading, and a voltage of minus several V to minus several hundreds of V relative to the electron source 7 is applied to the electrode 8. The electrode 9 functions as an ejecting electrode for ejecting electrons held by the grid (electrode 8), and a voltage of plus several hundreds of V to plus one thousand and several hundreds of V relative to the electron source 7 is applied to the electrode 9. In addition, the electrode 10 functions as a converging electrode for converging the electrons that have been ejected by the ejecting electrode (electrode 9) through the interaction with the below described fixed anode 12, and a voltage of plus several hundreds of V to plus one thousand and several hundreds of V relative to the electron source 7 is applied to the electrode 10.

The above described fixed anode 12 is provided between the target member 4 and the electrode 10 at the final stage from among the electrodes 8, 9 and 10. The fixed anode 12 has the grounded potential in the same manner as the target member 4, and a through hole 12a through which electrons pass is created at the center of the fixed anode 12, which is fixed to the main body portion 1a of the chamber through a support member 13. The electrons generated from the electron source 7 are electrostatically accelerated and converged by the electrical field within the vacuum chamber 1 by the electrodes 8, 9 and 10 as well as by the fixed anode so as to form an electron beam B, having a trajectory along the center axis Oa of the main body portion 1a of the chamber. The target member 4 having the ground potential is irradiated with the electron beam B, and as a result, the X-ray generated from the target 2 is lead to the outside through the X-ray emitting window 3.

In the above described embodiment, when the movable chamber portion 1b is made to make contact with the stopper 1c, the center of the target member 4 is located at a distance r away from the trajectory of the electron beam B along the center axis Oa of the main body portion 1a of the chamber. In this eccentric state, the point that is located at a distance r from the center of the target member 4 is irradiated with the electron beam B. A number of points for generating X-rays can be provided along an arc having a radius of r on the surface of the target 2 that is integrated with the lower surface of the target member 4 by changing the direction in which the movable chamber portion 1b shifts. In addition, the trajectory of the electron beam B does not change when the point for generating X-rays is changed.

Figure 2A:
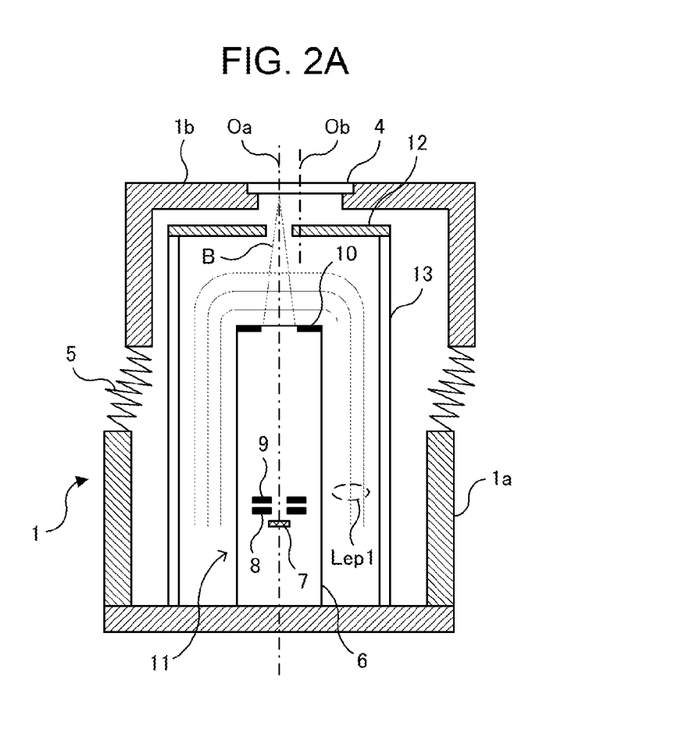
FIG. 2A is a diagram illustrating the form of the electrical field within the vacuum chamber as the target is shifted, which corresponds to the state in FIG. 1.

Namely, in the embodiment in FIG. 1, the form of the electrical field within the vacuum chamber 1 is determined by a cylinder 6 with the electrode 10 and the fixed anode 12 with support member 13, as shown by equipotential lines Lep1 in FIG. 2A, and therefore, the form of the electrical field within the vacuum chamber 1 does not change even when the position of the movable chamber portion 1b is changed. Accordingly, the trajectory of the electron beam B does not change when the movable chamber portion 1b is shifted. The absolute position of the point for generating X-rays does not shift either, and thus, the focal point does not shift.

Figure 2B:
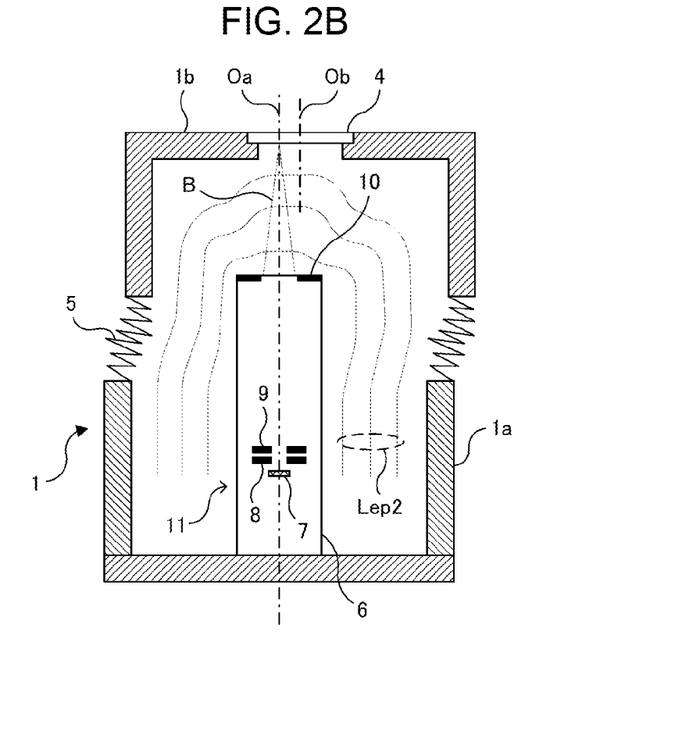
FIG. 2B is a diagram illustrating the form of the electrical field within the vacuum chamber as the target is shifted, which corresponds to the structure without any fixed anode.

In contrast, FIG. 2B shows equipotential lines Lep2 in the case where no fixed anode 12 or support member 13 is provided. In the case where no fixed anode 12 or support member 13 are provided, the form of the electrical field within the vacuum chamber 1 is determined by the cylinder 6 with the electrode 10 and the movable chamber portion 1b that includes the target member 4 forming the anode in this structure, and therefore, the form of the electrical field within the vacuum chamber 1 changes when the position of the movable chamber portion 1b is shifted. At the same time, the trajectory of electron beam B changes, and the absolute position of the point for generating X-rays is shifted and so is the focal point.

In the embodiment in FIG. 1, as described below, the focal point is not substantially shifted due to the increase in the temperature in the vicinity of the target member 4 after the usage over a long period of time.

Figure 3A:
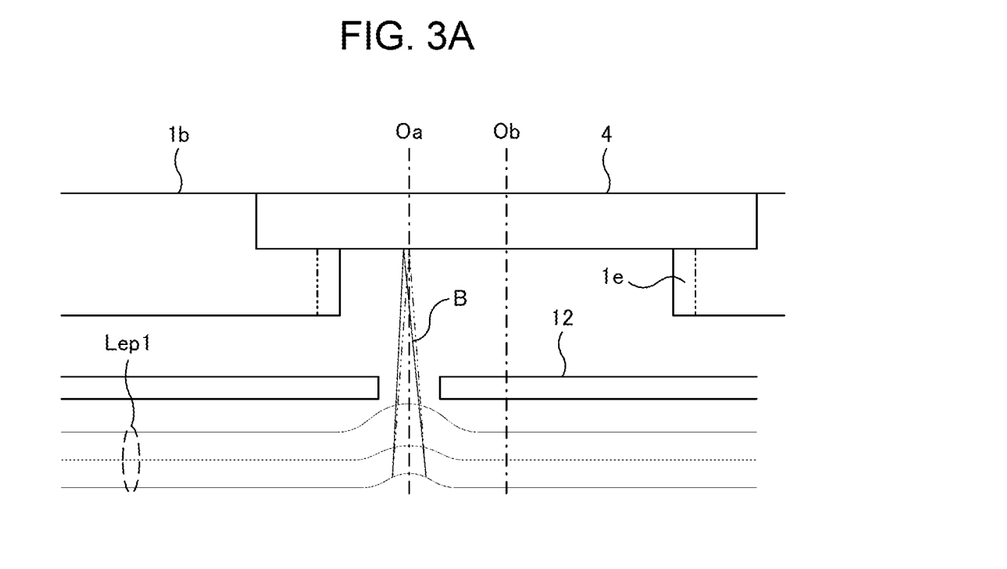
FIG. 3A is a diagram illustrating the form of the electrical field in the vicinity of the target after the usage over a long period of time in the structure in FIG. 1.

In the structure where the target member 4 is fixed to the vacuum chamber 1, a force is constantly applied to the target member 4 in the direction toward the inside of the vacuum chamber 1 when the inside of the vacuum chamber 1 is vacuumed. In addition, no structure needs to be provided outside the target member 4 in order to allow a subject to approach the target member 4 as close as possible. For these reasons, as shown in FIG. 3A, in general, the vacuum chamber 1 (movable chamber portion 1b) is provided with an inner flange 1e that protrudes from the lower side of the target member 4, so that the upper surface of the target member 4 and the upper surface of the vacuum chamber 1 (movable chamber portion 1b) can be in the same plane so as to provide a structure where the lower surface of the target member 4 is supported by the inner flange 1e. In an eccentric state where the movable chamber portion 1b has been shifted, the movable chamber portion 1b is located at a distance from trajectory of the electron beam B, which makes the unevenness inside the vacuum chamber 1 including the above described inner flange 1e asymmetrical with respect to the trajectory of the electron beam B at the center. When the structure inside the vacuum chamber 1 undergoes thermal expansion in this state, the positional relationships of the unevenness that is asymmetric with respect to the electron beam B change.

In the embodiment in FIG. 1, the fixed anode 12 is provided between the target member 4 and the electrode 10 so as to be fixed to the main body portion 1a or the chamber so that the form of the electrical field within the vacuum chamber 1 is determined by the fixed anode 12 and the electrodes 8, 9 and 10. Therefore, as shown in FIG. 3A, the equipotential lines Lep1 barely change within the vacuum chamber 1 even when the temperature of the target member 4 and its vicinity increases after the usage over a long period of time, which thermally expands the inner flange 1e as shown by the double dotted chain line. Therefore, the change in the trajectory of the electron beam B is practically to such an extend as to be negligible in this case, and thus, the focal point does not shift after the usage over a long period of time.

Figure 3B:
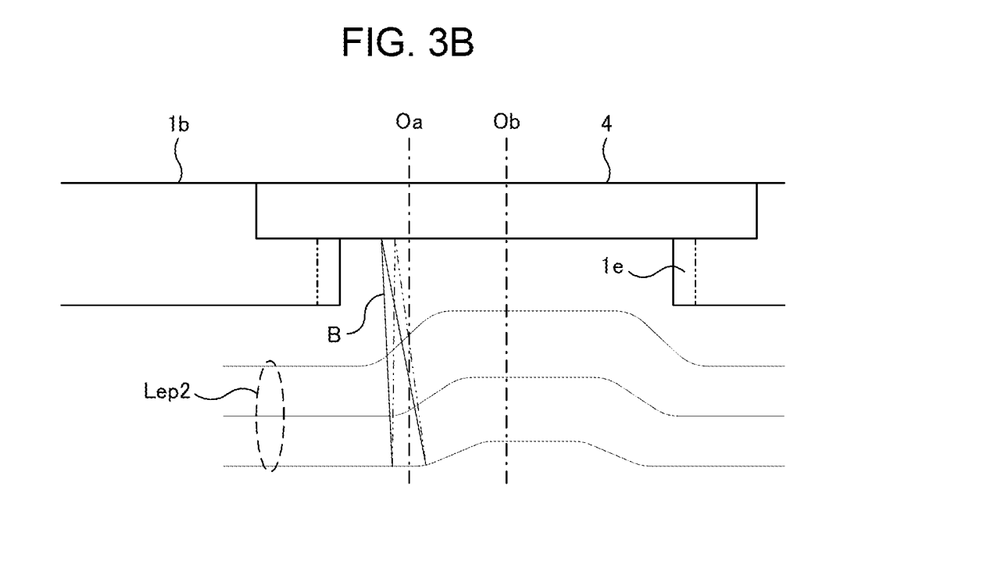
FIG. 3B is a diagram illustrating the form of the electrical field in the vicinity of the target after the usage over a long period of time in the structure without any fixed anode.

In contrast, in the case where there is no fixed anode 12, as shown in FIG. 3B, the unevenness of the member that substantially form the anode shifts asymmetrically with respect to the electron beam B, which changes the equipotential lines Lep2 when the temperature of the target member 4 and its vicinity increases as a result of the usage over a long period of time, which thermally expands the inner flange 1e as shown by the double dotted chain line. That is to say, the form of the electrical field changes and so does the trajectory of the electron beam B. As a result, the absolute position of the point for generating X-rays chronologically changes, which shifts the focal point when the apparatus is switched on so as to start generating X-rays.

Though in the embodiment in FIG. 1, the position of the fixed anode 12 is not particularly limited in the upward and downward directions, it is useful for the fixed anode 12 to be in close proximity to the target member 4 as in the figure in order to make the diameter of the spot of the electron beam B smaller on the surface of the target 2. The fixed anode 12 and the target member 4 are both grounded so as to have the same potential, and therefore, no electrical problem arises even when the two make contact with each other. Accordingly, it is desirable for the fixed anode 12 to be as close to the target member as possible.

In addition, a portion of the electron beam B with which the target 2 is irradiated is reflected so as to collide with the fixed anode 12, which generates X-rays. The X-rays may become a diminishing factor for the image quality in an X-ray apparatus for industrial use, and therefore, the smaller the amount of the X-rays is the more suitable the X-ray apparatus is for this use. It is desirable for the material of the fixed anode 12 at least in a range that has a possibility that the reflected electrons may collide with (may only on the surface) to be a light element substance such as beryllium, carbon or aluminum that generates a lower amount of X-rays.

Though in the above embodiment the focal point can be prevented from shifting while making it possible to provide a number of points for generating X-rays without reducing the degree of the vacuum inside the vacuum chamber by applying the present invention to the X-ray generator using a closed type vacuum chamber, the present invention is not limited to the use of a closed type vacuum chamber but can be applied to an X-ray generator using an open type vacuum chamber as log as the vacuum chamber is of such a type that electrons are electrostatically accelerated and converged by a group of electrodes.

EXPLANATION OF SYMBOLS vacuum chamber
1a main body portion of the chamber
1b movable chamber portion
2 target
3 X-ray emitting window
4 target member
5 linking member
6 cylinder
7 electron source
8 electrode (grid)
9 electrode (emitting electrode)
10 electrode (converging electrode)
11 electron gun
12 fixed anode
12a through hole
13 support

What is claimed is:

1. An X-ray generator, comprising: a vacuum chamber having an X-ray emitting window with which a target is integrated; and an electron source and a group of electrodes provided within the vacuum chamber, wherein each electrode has a predetermined potential difference relative to the electron source or the vacuum chamber so that electrons from said electron source are accelerated and converged by an electrical field created within the vacuum chamber so as to irradiate said target, and thus, X-rays can be generated so as to be taken out to the outside through said X-ray emitting window, characterized in that
   a portion of said vacuum chamber including said emitting window is linked to a main body portion of the vacuum chamber through a linking member so as to be movable, and
   an anode having a hole through which electrons transmit and having the same potential as the vacuum chamber is provided between the electrode at a final stage of said group of electrodes and said target within said vacuum chamber in such a state as to be fixed to the main body portion of the vacuum chamber.

2. The X-ray generator according to claim 1, characterized in that said anode is provided in close proximity to said target.

3. The X-ray generator according to claim 1, characterized in that a member made of a light element of which the atomic number is no greater than 13 is used for said anode in at least a range that has a possibility that reflected electrons may collide with.

4. The X-ray generator according to claim 1, characterized in that said linking member is a portion of the vacuum chamber including said X-ray emitting window, which is linked to said main body portion of the vacuum chamber so as to be translatable, and the portion of the vacuum chamber including said X-ray emitting window makes contact with the outside of said vacuum chamber, of which the contact state can be regulated so as to be translatable relative to said main body portion of the vacuum chamber by a regulating member that is provided outside the X-ray generator.

* * * * *